US00PP34590P2

(12) United States Plant Patent
van Sambeek

(10) Patent No.: US PP34,590 P2
(45) Date of Patent: Sep. 13, 2022

(54) ***LAVANDULA* PLANT NAMED 'DOLAVLADIETEL'**

(50) Latin Name: *Lavandula angustifolia*
Varietal Denomination: Dolavladietel

(71) Applicant: DUMMEN GROUP B.V., De Lier (NL)

(72) Inventor: Ellen van Sambeek, Oegstgeest (NL)

(73) Assignee: Dummen Group B.V., DeLier (NL)

( * ) Notice: Subject to any disclaimer, the term of this patent is extended or adjusted under 35 U.S.C. 154(b) by 0 days.

(21) Appl. No.: 17/695,229

(22) Filed: Mar. 15, 2022

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Lavandula* plant named 'Dolavladietel', characterized by its relatively compact, upright to outwardly spreading and uniformly mounded plant habit; vigorous growth habit and rapid growth rate; freely branching habit; early and freely flowering habit; dark violet-colored flowers positioned on strong peduncles; and good container and garden performance.

1 Drawing Sheet

Botanical designation: *Lavandula angustifolia.*
Cultivar denomination: 'DOLAVLADIETEL'.

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct *Lavandula* plant, botanically known as *Lavandula angustifolia*, commonly referred to as Lavender and hereinafter referred to by the name 'Dolavladietel'.

The new *Lavandula* plant is a product of a planned breeding program conducted by the Inventor in Aalsmeer, The Netherlands. The objective of the breeding program was to develop new unique *Lavandula* plants with long flowering period and attractive plant form and flower coloration.

The new *Lavandula* plant originated from an open-pollination in April, 2016 of a proprietary selection of *Lavandula angustifolia* identified as code number LV-0117, not patented, as the female, or seed, parent with an unknown selection of *Lavandula angustifolia* as the male, or pollen, parent. The new *Lavandula* plant was discovered and selected by the Inventor as a single flowering plant within the progeny of the stated open-pollination in a controlled environment in Aalsmeer, The Netherlands in April, 2017.

Asexual reproduction of the new *Lavandula* plant by terminal cuttings in a controlled greenhouse environment in Aalsmeer, The Netherlands since June, 2017 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Dolavladietel' as a new and distinct *Lavandula* plant:

1. Relatively compact, upright to outwardly spreading and uniformly mounded plant habit.
2. Vigorous growth habit and rapid growth rate.
3. Freely branching habit.
4. Early and freely flowering habit.
5. Dark violet-colored flowers positioned on strong peduncles.
6. Good container and garden performance.

Plants of the new *Lavandula* differ primarily from plants of the female parent selection primarily in the following characteristics:

1. Plants of the new *Lavandula* are more compact than and not as tall as plants of the female parent selection.
2. Plants of the new *Lavandula* flower earlier than plants of the female parent selection.

3. Plants of the new *Lavandula* have smaller flowers than plants of the female parent selection.

Plants of the new *Lavandula* can be compared to plants of the *Lavandula angustifolia* 'Essence Purple', not patented. In side-by-side comparisons, plants of the new *Lavandula* differ primarily from plants of 'Essence Purple' in plant size as plants of the new *Lavandula* are more compact than and not as tall as plants of 'Essence Purple'. In addition, plants of the new *Lavandula* flower earlier than plants of 'Essence Purple'.

BRIEF DESCRIPTION OF THE PHOTOGRAPH

The accompanying photograph illustrates the overall appearance of the new *Lavandula* plant showing the colors as true as it is reasonably possible to obtain in colored reproductions of this type. Colors in the photograph may differ slightly from the color values cited in the detailed botanical description which accurately describe the colors of the new *Lavandula* plant.

The photograph is a side perspective view of a typical flowering plant of 'Dolavladietel' grown in a container.

DETAILED BOTANICAL DESCRIPTION

The aforementioned photograph and following observations and measurements describe plants grown in 17-cm containers in Aalsmeer, The Netherlands during the summer initially in a glass-covered greenhouse and finished in an outdoor nursery and under conditions and cultural practices which approximate those generally used in commercial *Lavandula* plant production. During the production of the plants, day temperatures averaged 21° C. and night temperatures averaged 15° C. Plants were 26 weeks old when the photograph and description were taken. In the following description, color references are made to The Royal Horticultural Society Colour Chart, Second Edition, except where general terms of ordinary dictionary significance are used. Measurements represent averages for typical flowering plants.

Botanical classification: *Lavandula angustifolia* 'Dolavladietel'.

Parentage:

*Female, or seed, parent*.—Proprietary selection of *Lavandula angustifolia* identified as code number LV-0117, not patented.

*Male, or pollen, parent*.—Unknown selection of *Lavandula angustifolia*, not patented.

Propagation:

*Type*.—Terminal vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Medium in thickness, fibrous; typically white to light yellow in color, actual color of the roots is dependent on substrate composition, water quality, fertilizer type and formulation.

*Rooting habit*.—Moderately freely branching; medium density.

Plant description:

*Plant and growth habit*.—Herbaceous perennial; good performance as a container and as a garden plant; relatively compact, upright to outwardly spreading and uniformly mounding plant habit; vigorous growth habit and rapid growth rate; flowers arranged in verticillasters on crowded spikes.

*Plant height, soil level to top of floral plane*.—About 30 cm.

*Plant width*.—About 48 cm.

*Lateral branch description*.—Quantity per plant: Freely branching with about 18 primary lateral branches each with about three secondary lateral branches developing per plant. Length: About 32 cm. Diameter: About 4 mm. Internode length: About 1.5 cm. Strength: Strong. Aspect: Erect to about 70° from vertical. Texture and luster: Pubescent; glossy; becoming woody and glabrous with development. Color, when developing: Close to 145A. Color, developed: Close to 144B; when becoming woody, close to 199A.

*Leaf description*.—Arrangement: Opposite and decussate, simple; sessile. Length: About 3.5 cm. Width: About 5 mm. Shape: Linear to lanceolate. Apex: Obtuse. Base: Cuneate. Margin: Entire. Texture and luster, upper surface: Pubescent; glossy. Texture and luster, lower surface: Pubescent; matte. Fragrance: Strongly aromatic, pungent. Venation pattern: Pinnate. Color: Developing and fully expanded leaves, upper surface: Close to 137A; venation, close to 137A. Developing and fully expanded leaves, lower surface: Close to 137C; venation, close to 137C.

Flower description:

*Flower type, arrangement and habit*.—Single bilabiate flowers arranged in compact verticillasters on crowded terminal spikes; freely flowering, about 33 flowers per inflorescence and about 6,138 flowers developing per plant; flowers with two-lobed upper lip and three-lobed lower lip; flowers face mostly outwardly on the spike.

*Natural flowering season*.—Flowering is continuous from June to August in The Netherlands; plants begin flowering about twelve weeks after planting.

*Flower longevity on the plant*.—Inflorescences last about three to four weeks on the plant; flowers persistent.

*Fragrance*.—Strongly fragrant; typical lavender scent.

*Flower buds*.—Length: About 5 mm. Diameter: About 2 mm. Shape: Elliptic. Texture and luster: Pubescent; matte. Color: Close to 83A.

*Inflorescence size*.—Length: About 3 cm. Diameter: About 2 cm.

*Flower size*.—Diameter: About 6 mm by 7 mm. Depth (height): About 1 cm. Throat diameter: About 4 mm. Tube length: About 2 mm. Tube diameter: About 2 mm.

*Petals*.—Quantity and arrangement: Upper lip, two-lobed and lower lip, three-lobed. Length: About 3 mm. Width: About 2 mm. Shape: Linear; proximally, fused into a tube. Apex: Obtuse, rounded. Margin: Entire; not undulate. Texture and luster, upper and lower surfaces: Smooth, glabrous; matte. Texture, throat and tube: Smooth, glabrous; matte. Color: When opening and fully opened, upper surface: Close to 86B; venation, close to 86B; color does not change with subsequent development. When opening and fully opened, lower surface: Close to 86B; venation, close to 86B; color does not change with subsequent development. Throat: Close to 85A; venation, close to 85A. Tube: Close to 86B; venation, close to 86B.

*Basal flower bracts*.—Quantity and arrangement: Subtending the flowers is a single basal flower bract. Length: About 5 mm. Width: About 3 mm. Shape: Aristate. Margin: Entire. Texture, upper and lower surfaces: Smooth, glabrous. Color, upper and lower surfaces: Close to 144B.

*Sepals*.—Quantity and arrangement: Five, fused forming a tubular calyx. Length: About 5 mm. Width: About 1 mm. Shape: Linear. Apex: Obtuse. Margin: Entire. Texture and luster, upper surface: Pubescent; matte. Texture and luster, lower surface: Smooth, glabrous; semi- glossy. Color: When opening and fully opened, upper surface: Close to 86A. When opening and fully opened, lower surface: Close to 144A.

*Pedicels*.—Length: About 1 mm. Diameter: About 1 mm. Strength: Weak. Texture and luster: Pubescent; matte. Color: Close to 155D.

*Reproductive organs*.—Stamens: Quantity per flower: Four. Filament length: About 2 mm. Filament color: Close to 155D. Anther shape: Reniform; dorsifixed. Anther size: About 1 mm by 1 mm. Anther color: Close to 200B. Pollen amount: Moderate. Pollen color: Close to 23A. Pistils: Quantity per flower: One. Pistil length: About 4 mm. Stigma shape: Capitate. Stigma diameter: About 0.5 mm. Stigma color: Close to 86A. Style length: About 2 mm. Style color: Close to 144D. Ovary color: Close to 144A.

*Seeds and fruits*.—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain, wind and to tolerate temperatures ranging from about −34° C. to about 35° C. and to be suitable for USDA Hardiness Zone 5.

It is claimed:

1. A new and distinct *Lavandula* plant named 'Dolavladietel' as illustrated and described.

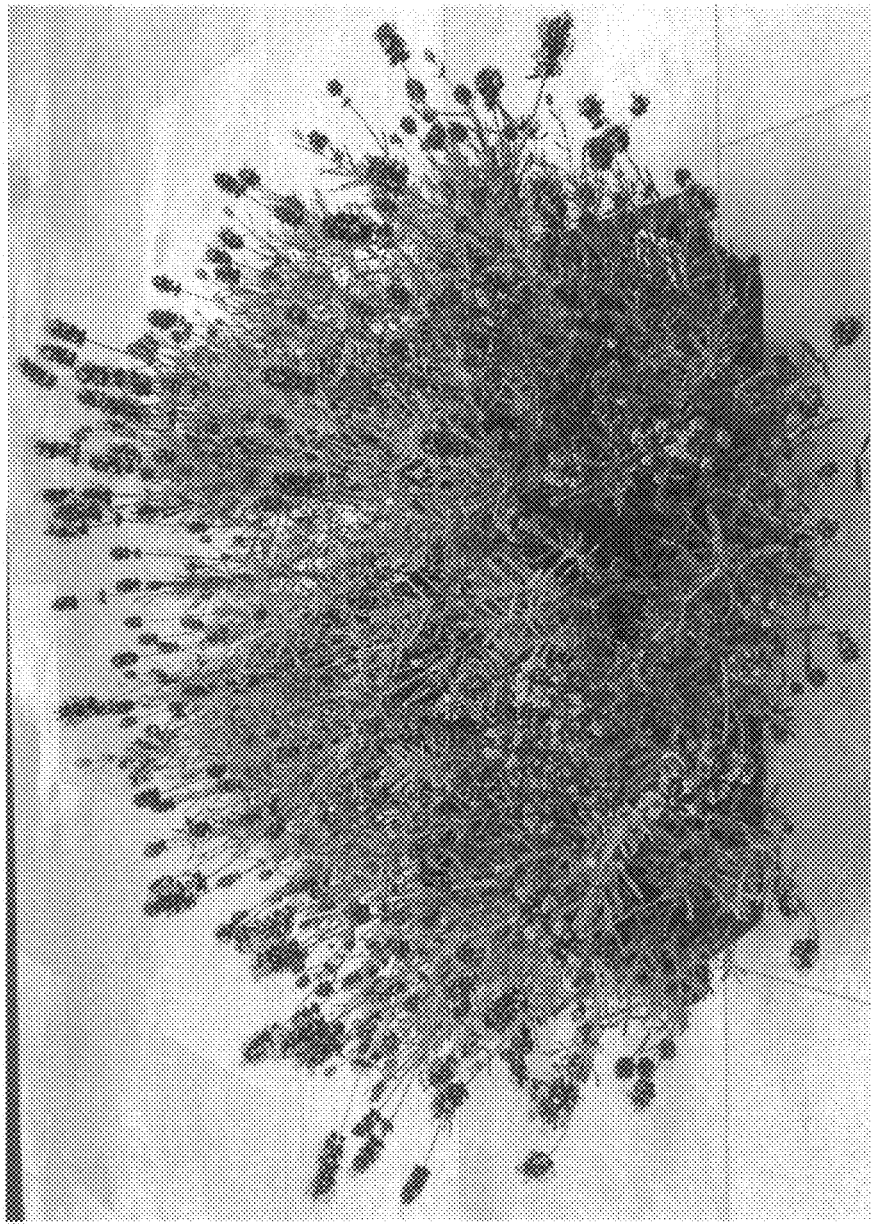

* * * * *